United States Patent [19]
Rudolph

[11] Patent Number: 5,265,595
[45] Date of Patent: Nov. 30, 1993

[54] MASK FOR BREATH ANALYSIS

[75] Inventor: Kevin A. Rudolph, Kansas City, Mo.

[73] Assignee: Hans Rudolph, Inc., Kansas City, Mo.

[21] Appl. No.: 28,720

[22] Filed: Mar. 9, 1993

Related U.S. Application Data

[63] Continuation of Ser. No. 654,791, Feb. 12, 1991, abandoned, which is a continuation-in-part of Ser. No. 644,429, Jan. 22, 1991, abandoned, which is a continuation of Ser. No. 367,775, Jun. 19, 1989, abandoned.

[51] Int. Cl.$^5$ ............................................. A61M 16/00
[52] U.S. Cl. .......................... 128/204.18; 128/204.33; 128/205.25
[58] Field of Search ....................... 128/204.18, 205.25, 128/207.11, 204.23; 24/178, 188, 585, 616

[56] References Cited

U.S. PATENT DOCUMENTS

| | | | |
|---|---|---|---|
| 2,449,053 | 9/1948 | Burs et al. | 73/40 |
| 3,232,288 | 2/1966 | Krobath | 128/724 |
| 3,420,224 | 1/1969 | Farr | 128/719 |
| 3,486,366 | 12/1969 | Jackson | 73/40 |
| 3,580,051 | 5/1971 | Blevins | 73/40 |
| 4,171,555 | 10/1979 | Bakker | 24/200 |
| 4,414,973 | 11/1983 | Matheson et al. | 128/206.15 |
| 4,519,399 | 5/1985 | Hori | 128/724 |
| 4,674,492 | 6/1987 | Niemeyer | 128/202.22 |
| 4,765,325 | 8/1988 | Crutchfield | 128/202.13 |
| 4,846,166 | 7/1989 | Willeke | 128/200.24 |
| 4,914,957 | 4/1990 | Dougherty | 73/40 |
| 4,960,121 | 10/1990 | Nelson et al. | 128/207.11 |

FOREIGN PATENT DOCUMENTS

| | | |
|---|---|---|
| 950429 | 10/1956 | Fed. Rep. of Germany ...................... 128/207.11 |
| 780746 | 5/1935 | France ........................... 128/207.11 |

OTHER PUBLICATIONS

"Measurement-Dioxide"; Burton; Br. II of Anesthsia; 1969 41:723-30.
"Validation . . . Swine"; McKernan et al; J. Appl Phys.; 1986 Sep. 61(3) 1226-9.
"Human . . . a Low Oz"; Hersch et al; I. Appl. Phys.; 1982 Nov. 53(5) 1281-90.
"Gen Product Info . . . Model #7200"; Hans Rudolph, Inc. Product Sheet; Dec. 1984.
"Nutrictional Assesement . . . Handbook"; D. Zavale; Copy right 1989 pp. 55-56.

*Primary Examiner*—Edgar S. Burr
*Assistant Examiner*—Aaron J. Lewis
*Attorney, Agent, or Firm*—Litman, McMahon & Brown

[57] ABSTRACT

An oral respiratory mouth mask for breath-by-breath ventilatory measurements on humans constructed of silicone or like material. The mouth mask has a curved face sealing flange adapted to sealably engage the user's skin about the mouth and nose including an internal mouth-enclosing chamber having a relatively small dead space within the mask for improved accuracy in ventilatory and metabolism measurements. A direction airflow tubing assembly secured to and in flow communication with the mouth-enclosing chamber operates to effectively direct exhalation products and inhaled air while producing minimum restrictions to normal airflow. The mask is held in a sealed position about a user's mouth by a securing assembly comprising a flexible skull cap, adjustable elastic straps and quick connect fasteners which cooperate with pendulatory eccentric buttons integrally formed on the outer surface of the face mask.

4 Claims, 2 Drawing Sheets

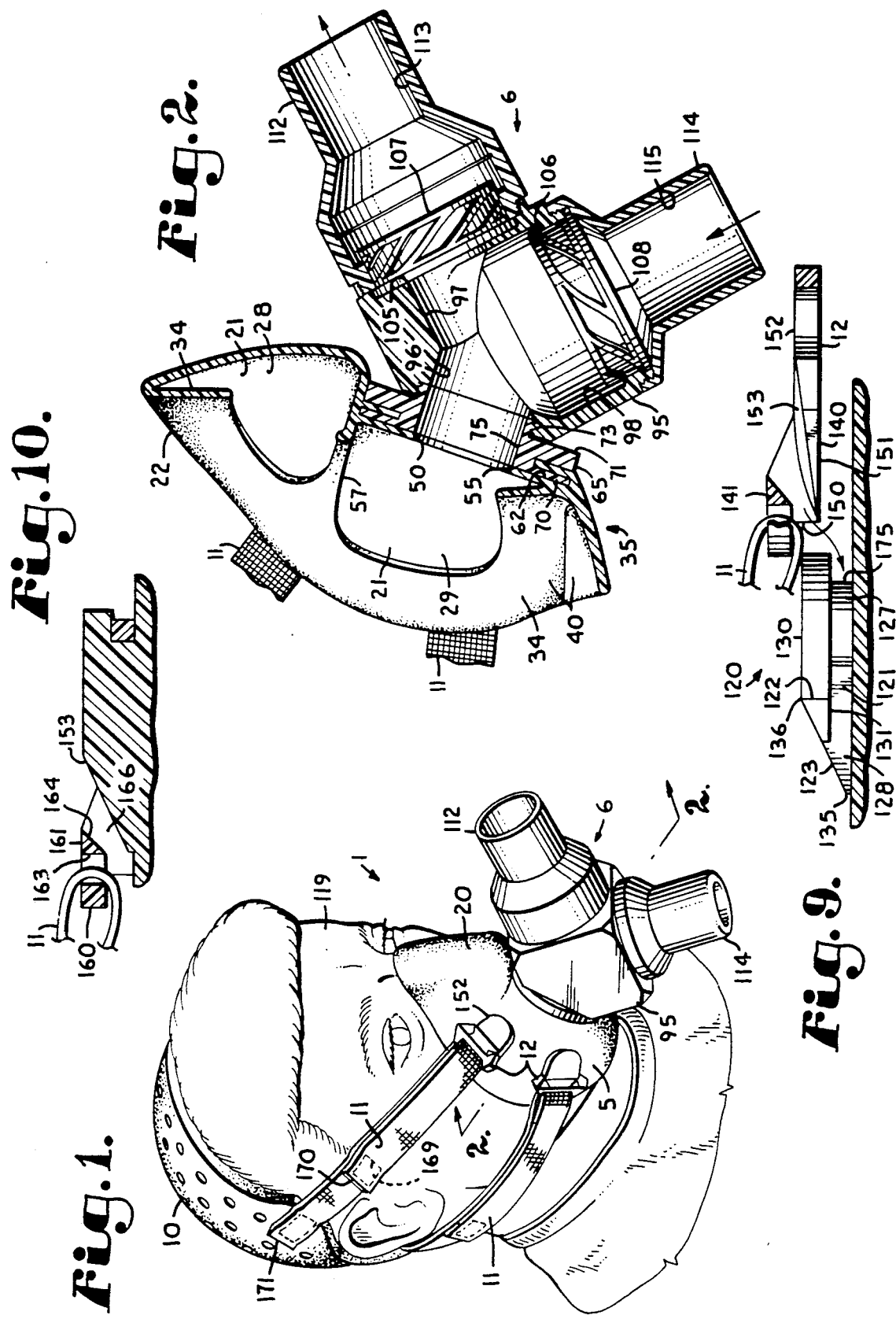

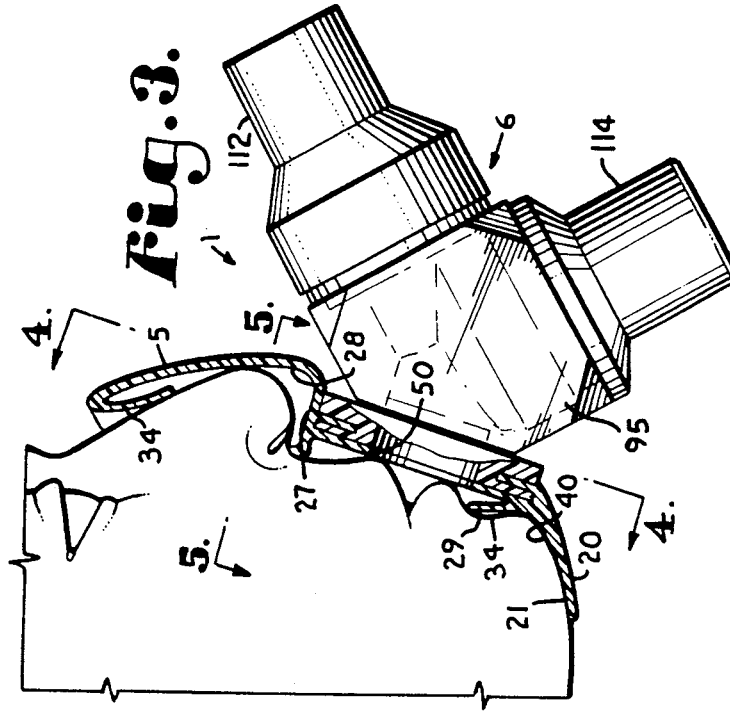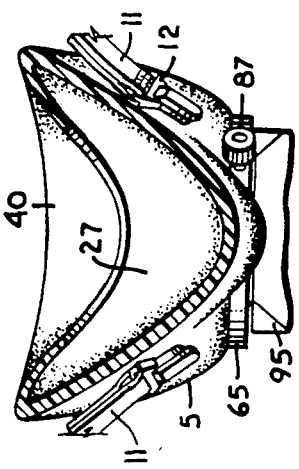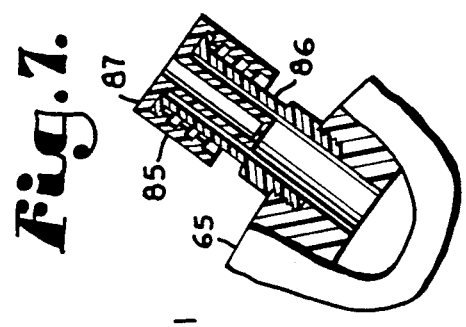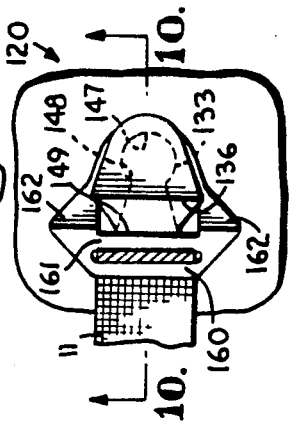

MASK FOR BREATH ANALYSIS

CROSS-REFERENCE TO RELATED APPLICATION

This a continuation of U.S. patent application Ser. No. 07/654,791, filed Feb. 12, 1991, now abandoned entitled IMPROVED MASK FOR BREATH ANALYSIS which was a continuation-in-part of U.S. patent application Ser. No. 07/644,429, filed Jan. 22, 1991, now abandoned entitled RESPIRATORY MASK which was a continuation of Ser. No. 07/367,775, filed Jun. 19, 1989, now abandoned entitled RESPIRATORY MASK.

BACKGROUND OF THE INVENTION

This invention relates to an oral respiratory mask to provide breath-by-breath measurements of respiration and metabolism in adults or children. In particular, the invention relates to such a mask having minimum dead space, so as to improve the analytic quality of such measurements.

Breath-by-breath measurements of respiration and metabolism are useful in determining the over-all health or fitness of an individual and also in the identification of specific illnesses, especially illnesses related to the pulmonary and cardiovascular systems.

Typical measurements include measurements of such parameters as breath-by-breath volume, temperature, and exhaled gas composition. The volume of air measured is the volume which enters and leaves the lungs with each breath, which volume is referred to as tidal volume. Composition measurements typically include measurements such as percentage of carbon dioxide or moisture. Temperature measurements may include measurements of the temperature of air inhaled or exhaled with each breath.

Relatively high accuracy in the measurements of such parameters is required if the measurement is to be useful as an indicator of health or illness. If a parameter cannot be detected with relative accuracy and, thus, with certainty, an individual's health may not be properly assessed or an illness may go undetected. Thus, it is preferable for a mask used to make respiratory measurements to provide measurements of respiratory parameters that are as accurate as possible. Further, modern technology in analysis of exhaled gases has exceeded the ability of conventional mouth covering masks to provide satisfactory samples to the analysis equipment.

Conventional face masks used to measure respiratory parameters on a breath-by-breath basis inherently produce inaccurate measurements because the face masks have excessive dead space within the mask. Dead space is that space or cavity volume formed between the skin surface of the user within the mask and the internal surface or walls of the mask. While a small volume of dead air space will not normally cause appreciable inaccuracy in measurement, the dead space in conventional mouth covering masks is excessive and results in carbon dioxide rebreathing and other alterations in ventilatory response that provide somewhat inaccurate measurements. Further, where parameters are changing quickly, dead space may result in gasses from previous breaths being analyzed, as if such gasses were currently being exhaled, which can result in relevant analytical errors. Because compensation for the effects on measurements caused by rebreathing or ventilatory response alternations cannot usually be made, excessive dead air space results in a failure to accurately assess an individual's state of health.

Conventional face masks having excessive dead space typically have been of a design which enclosed a user's nose and mouth. Attempts have been made to lessen dead space associated with the mask by providing a breathing device for enclosing only the mouth, thus eliminating the dead space otherwise present in the proximity of the nose. However, such prior devices for only the mouth did not provide an adequate face seal and, thus, were eventually designed to be inserted in the user's mouth, held in position by the user's teeth with the user's lips acting as a seal. Even the mouth-held versions were often ineffective or completely unusable because the user's jaw and facial muscles would soon tire, reducing the effectiveness of the device. Such mouth-held devices were basically unusable by the infirm, who often require testing of this type, and by children.

The present invention overcomes the problems associated with excessive dead air space by providing a respiratory mask of a design minimizing the dead air space, yet effectively sealing with the face of the user. Moreover, the present invention provides a mask which, because of its curvature and flexibility, may be used to provide highly accurate breath-by-breath measurements of respiration and metabolism in adults and children.

SUMMARY OF THE INVENTION

The present invention consists primarily of a respiratory mask having a relatively very small minimum dead air space, a unique directional airflow regulating system and a face-sealing surface constructed for superior facial fit on both adults and children. The respiratory mask is fabricated from silicone or other like material having both flexibility and resilience for improved sealing qualities, while producing relatively very little skin irritation.

More specifically, a sealing flange associated with the respiratory mask has a face-sealing surface adapted to form a seal that fits snugly against the surface of the user's face around the user's oral and nasal passages, providing an improved comfort fit in addition to a positive/negative pressure seal.

A common airflow passageway extends through the mask generally in alignment with the direction of airflow into and out of the mouth. The airflow passageway flow communicates with an inhalation and exhalation valve housing secured to a frontal surface of the mask and having a single airflow passageway extending therethrough, such that a common airflow passageway extension bifurcates or branches out into an inhalation passageway and an exhalation passageway. One way check valves for controlling the direction of airflow through the inhalation and exhalation valve housing extend across the inhalation passageway and the exhalation passageway. Inhaled gasses pass through the inhalation passageway only, then into the common airflow passageway and into a chamber formed by the mask for inhalation by a mask wearer. Upon exhalation, exhalation products are released into the mask and pas through the common airflow passageway and then out the exhalation passageway only.

The inhalation and exhalation valve housing may include sampling ports which are flow-connected to sampling lines. The inhalation passageway and exhalation passageway may communicate with a supplied breathing gas stream and/or exhaled gas analysis equipment, respectively. The fit of the mask against the face of a wearer is such that the dead space volume of the chamber formed by the mask is minimal. The wearer inhales and exhales directly from and into the chamber formed by the mask directly in front of and into the common airflow passageway. Inhalation gasses and exhalation products both pass through the common airflow passageway.

Connecting posts extend from the frontal surface of the mask and cooperate with straps which are secured to an extend forwardly from a skull cap positionable on the crown of a wearer's head to sealably secure the mask to the user. The straps are adjustable to maintain a firm, but comfortable, mask fit and facial seal. The straps attach to the cap in such a manner as to position the straps for improved comfort and reduction of tension and pain created by conventional masks. A fastener secured to the end of each of the straps functions in cooperation with the posts to facilitate attaching or removing the straps from the mask.

The dead space in a cavity formed within the mask during use is minimal. The cavity is sized and shaped to allow proper inlet and outlet gas flows relative to the user and sufficient spacing to accommodate the lips, etc. of the user, but otherwise effectively includes little, if any, additional volume.

OBJECTS AND ADVANTAGES OF THE INVENTION

Therefore, the objects of the present invention are: to provide a respiratory mask for use in breath-by-breath measurements of respiration and metabolism which produces improved accuracy because of minimal dead space associated therewith; to provide such mask with a superior configuration which can flexibly, but firmly, conform to the shape of a user's face; to provide such a face mask which is effective for use on adults or children; to provide such a mask that can be passively used by a person to be tested without requiring the person to actively hold the mask in place or seal about the mask; to provide such a mask that effectively directs respiratory gasses into and out of a respiratory monitoring system while producing minimal restrictions or impediments to normal breathing; to provide such a mask that has a head securing system including a cap and straps configured to be comfortable to the user and reduce pain and tension to the user as compared to conventional masks; to provide such mask including attachment member for connecting the straps to the mask that allow quick and simple connection to facilitate use of the mask; and to provide such a mask which is relatively inexpensive to produce, easy to use and particularly adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a respiratory apparatus of the present invention, shown worn by a user.

FIG. 2 is an enlarged and fragmentary, cross-sectional view of the respiratory apparatus, taken along line 2—2 of FIG. 1.

FIG. 3 is an enlarged, side elevational view of the respiratory apparatus with portions broken away to show interior details thereof.

FIG. 4 is a fragmentary and enlarged, cross-sectional view of the respiratory apparatus, taken along line 4—4 of FIG. 3.

FIG. 5 is an enlarged and fragmentary, cross-sectional view of the respiratory apparatus, taken along line 5—5 of FIG. 3

FIG. 6 is an enlarged and fragmentary, cross-sectional view of the respiratory apparatus, taken along line 6—6 of FIG. 4.

FIG. 7 is an enlarged and fragmentary view of a sample port extending outwardly from the respiratory apparatus, with portions broken away to show interior detail thereof.

FIG. 8 is an enlarged and fragmentary view of the respiratory apparatus, showing a securing strap fastener secured to a securement button.

FIG. 9 is an enlarged and fragmentary view of the respiratory apparatus with portions broken away to show the cooperation between the securement strap fastener and the securement button.

FIG. 10 is an enlarged and fragmentary, cross-sectional view of the respiratory apparatus, taken along line 10—10 of FIG. 8, showing the securement strap fastener secured to the securement button.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching on skilled in the art to variously employ the present invention in virtually any appropriately detailed structure.

Referring to the drawings in more detail, the reference numeral 1 generally represents a respiratory apparatus of the present invention. The respiratory apparatus 1 generally comprises a face mask or face piece 5, an airflow tubing assembly 6 and a face mask securing mean which in the illustrated embodiment comprises a flexible skull cap 10, adjustable securement straps 11 and strap fasteners 12.

The face mask 5 is constructed of silicone or other like material that is preferably flexible and yet resilient and that does not cause substantial skin irritation to the user. The face mask 5 is a cup-like structure having an outer surface 20 and an inner surface 21 and positionable on the face of a user so as to generally encircle and enclose the nose and mouth of the user. An endless outer peripheral edge 22 of the face mask 5 is shaped to conform with the shape of the face of an average user of the mask and generally conforms to the shape of the face upon which the mask 5 is secured.

A separating wall 27 extends across the inner surface of the face mask 5 so as to separate the volume enclosed by the mask 5 when secured to a wearer's face into a nose-enclosing chamber 28 and a mouth-enclosing chamber 29. The mask 5 includes sealing means, such as a sealing flange 34, which is integrally formed with and extends inwardly from the peripheral edge 22 of the mask 5, except at a lower portion 35 thereof, so as to extend partially over the area enclosed by the mask 5 in spaced relation with the inner surface 21 of the mask. At the lower portion 35 of the peripheral edge 22, the sealing flange 34 extends across the inner surface 21 of the face mask 5 so as to be spaced inwardly away from the peripheral edge 22 such that generally at the lower portion 35 of the peripheral edge 22 the inner surface 21 of the mask 5 and the sealing flange 34 form a chin receiving surface 40 adapted to conform to the shape of a user's chin positioned thereagainst.

The sealing flange 34 comprises a thin layer of the flexible and resilient material used to construct the rest of the face mask 5. The sealing flange 34 generally forms a continuous compound curve adapted to conform to the shape of a face upon which the mask is secured. As the mask 5 is pulled against the face of a wearer, the flange 34 is pressed towards the inner surface 21 of the mask 5 so as to reduce the volume of space between the flange 34 and the inner surface 21. The inherent resiliency of the flange 34 biases the flange 34 into sealing engagement with the face of the wearer. When the face mask 5 is abuttingly positioned against the face of a user the sealing flange 34 and the separating wall 27 cooperate to encircle and form separate airtight seals around the nose and the mouth of the user, such that the nose-enclosing chamber 28 does not flow communicate with the mouth-enclosing chamber 29. The resiliency and flexibility of the flange 34 allow the face mask 5 to conform to the shape of the face of various users.

A circular opening 50 extends through the face mask 5 so as to flow communicate with the mouth-enclosing chamber 29. The opening 50 is generally positioned so as to be aligned with the mouth of a user when the mask 5 is abuttingly positioned against the face of a user. The opening 50 is further sized so as to generally encircle the opening formed by the mouth of the user when the mouth is used for breathing during ventilatory measurement and analysis procedures.

The opening 50 is defined by a grooved circular shoulder 55, extending through the face mask 5 from the inner surface 21 to the outer surface 20. A rim receiving groove 62 extends into the mask 5 along the grooved circular shoulder 55.

The airflow tubing assembly 6 is connected to the face mask 5 at the circular opening 50 by an annular connecting member 65. The annular connecting member 65 includes a connecting rim 70, a first collar 71 and a threaded collar 73. A common airflow passageway 75 extends through the annular connecting member 65.

The connecting rim 70 of the annular connecting member 65 is snugly securable within the rim receiving groove 62 in the mask 5 so as to removably secure the annular connecting member 65 to the mask 5. When the annular connecting member 65 is secured to the mask 5 the common air flow passageway 75 generally extends through the opening 50.

A sampling port 85 extends through the first collar 71 to the common air flow passageway 75. A threaded tube 86 is secured to the first collar 71 in flow communication with the sampling port 85 and extends outward from the second collar 72. The threaded tube 86 threadingly receives a sealing cap 87 for sealably closing the sampling port 85.

A Y-branch tube member 95 having a common airflow passageway extension 96, an exhalation airflow passageway 97 and an inhalation airflow passageway 98 is threadingly secured to the threaded collar 73 of the annular connecting member 65. When the Y-branch tube member 95 is secured to the annular connecting member 65, the common airflow passageway extension 96 extends in axial and adjacent alignment with the common airflow passageway 75 so as to be in flow communication therewith. The exhalation airflow passageway 97 and the inhalation airflow passageway 98 branch out from the common airflow passageway 96 generally at 45° angles thereto so as to extend in perpendicular alignment with respect to one another.

The exhalation airflow passageway 97 ends at an exhalation valve opening 105 and the inhalation airflow passageway 98 ends at an inhalation valve opening 106. Airflow regulation means, such as an exhalation check valve assembly 107 of the type illustrated in U.S. Pat. No. 3,902,516 (which is incorporated herein by reference), extends across the exhalation valve opening 105 and airflow regulation means, such as an inhalation check valve assembly 108 of the type illustrated in U.S. Pat. No. 3,902,516, extends across the inhalation valve opening 106.

An exhalation discharge tube 112 having an exhalation discharge passageway 113 extending therethrough is threadingly secured to the Y-branched tube 95 so that the exhalation discharge passageway 113 extends in axial alignment and in flow communication with the exhalation airflow passageway 97. Similarly, an inhalation intake tube 114 having an inhalation intake passageway 115 extending therethrough is threadingly secured to the Y-branched tube 95 so that the inhalation intake passageway 115 extends in axial alignment and in flow communication with the inhalation airflow passageway 98. Both the exhalation discharge tube 112 and the inhalation intake tube 114 are designed to cooperate with respiratory monitoring equipment.

The outer surface 20 of the face mask 5 includes four strap securing buttons 120 extending outward therefrom. The buttons 120 are adapted to quickly and removably receive the strap fasteners 12 which cooperate with the adjustable securement straps 11 and the skull cap 10 to secure the face mask 5 in place against a face 119 of a user.

The strap securing buttons 120 are integrally formed of the same flexible material as the rest of the mask 5 and comprise a post 121, a circumferential flange or enlarged head 122 and an eccentric cam surface 123. The post 121 extends perpendicularly away from the outer surface 20 of the mask 5 and is generally keyhole shaped having a circular portion 127 and a triangular or outwardly flared portion 128 extending therebehind. The enlarged head 122, having an upper surface 130 and a lower surface or overhanging edge 131, generally extends over the circular portion 127 of the post 121. The cam surface 123 angles upwards and extends from the outer surface 20 of the mask 5 along a rear edge 135 of the outwardly flared portion 128 of the post 121 to a rear edge 136 of the upper surface 130 of the enlarged head 122.

Each of the strap fasteners 12 comprises a post encircling structure 140 and a strap securing structure 141. The post encircling structure 140 includes a cutaway post receiving opening comprising a circular cutaway portion 147, a straight cutaway portion 148 and an outwardly flared cutaway portion 149 generally corresponding to the shape of the post 121. The post encircling structure 140 includes an open end 150, a lower surface 151, an upper surface 152 and an inclined surface 153. The inclined surface 153 extends upwards from the lower surface 151 to the upper surface 152 of the post enclosing structure 140 generally along the outwardly flared cutaway portion 149.

The strap securing structure 141 comprises a rear crossmember 160 and a forward crossmember 161 positioned slightly above the post encircling structure 140 by support members 162 and extending across the open end 150 of the post encircling structure 140. Rear crossmember 160 and forward crossmember 161 are spaced apart to form a strap receiving aperture 163 therebetween. The forward crossmember 161 has an upwardly angled lower surface 164. An upwardly angled passageway 166 extends between the upwardly angled lower surface 164 of the strap retaining structure 141 and the inclined surface 153 of the post encircling structure 140.

A free end 170 of each of the adjustable securement straps 11, secured at an opposite end 171 to the skull cap 10, is threaded through a strap receiving aperture 163 in one of the strap fasteners 12 and doubled back to form a loop and secured in place by a securement means such as a hook and loop type fastener 169 of the type sold under the tradename Velcro. The free end 170 of one of the straps 11 is secured using the fastener 169 generally at any position along the length of the strap 11, such that the length of the strap 11 from the cap 10 to the mask 5 is adjustable. The strap 11 is preferably constructed of a elastic material.

Each strap fastener 12 is secured to a respective strap securing button 120 by initially advancing the open end 150 of the post encircling structure 140 towards a leading edge 175 of the post 121. As the post encircling structure 140 is advanced into encircling relationship with the post 121, the enlarged head 122 is directed by the inclined surface 153 through the upwardly angled passageway 166. As the portion of the post encircling structure 140 adjacent the straight cutaway portion 148 advances past the circular portion 127 of the post 12 the circular portion 127 of the post 121 is compressed. As the circular cutaway portion 147 is advanced into alignment with the circular portion 127 of the post 121, the circular portion 127 of the post 121 expands to secure the fastener 12 in place with the lower surface 131 of the enlarged head 122 in abutting relationship with the upper surface 152 of the post encircling structure 140 of the fastener 12.

When the fastener 12 is removed from the button 120, the fastener 12 is advanced so that the upwardly angled lower surface 164 of the forward crossmember 161 engages the inclined surface 153 of the button 120 so as to direct the strap retaining structure 141 over the upper surface 130 of the enlarged head 122. The fastener 12 is then advanced out of engaging relationship with the button 120.

The cap 10 is positioned on a user so as to encircle the crown of the user's skull. Four straps 11 extend from the cap 10 to the four buttons on the mask 5. One pair of straps 11 extends from opposing sides of the cap so as to extend just above the ears of the user to opposing sides of the mask 5. A second pair of straps extends from a opposing sides of the cap 10 at a lower edge so as to extend close to but below the ears of the user to opposing sides of the mask 5. The cap spreads the pulling force from the straps generally across the entire crown of the user and the lower straps 11 are positioned in use generally above a user's neck so that the mask is generally supported completely by the user's skull crown rather than the user's neck. The buttons 120 are positioned on the mask 5 such that the straps pull the mask 5 against the users face along the chin and the upper lip region.

When the mask 5 is positioned against the face of a user and the straps 11 are appropriately adjusted, the straps 11 pull the mask 5 against the face so as to generally advance the sealing flange 34 against the inner surface 21 of the mask 5 so as to significantly reduce the amount of dead space in the mouth-enclosing chamber 29 while forming an airtight seal between the sealing flange 34 and the face of the user. The mask 5 is positioned so that the mouth opening of the user is flow aligned with the circular passageway 50 in the mask 5 and the common airflow passageway 96 in the airflow tubing assembly 6. The nose of the user is completely enclosed in the nose-enclosing chamber 28 of the mask 5 so as to prevent the patient from breathing through their nose.

As the wearer of the apparatus 1 inhales, the negative pressure pulls the inhalation valve assembly 108 open allowing air to travel through the inhalation intake passageway 115, through the inhalation valve opening 106, through the inhalation airflow passageway 98, through the common airflow passageway extension 96 through the common airflow passageway 75 through the mask 5 and into the mouth of the wearer. The negative pressure of inhalation holds the exhalation valve assembly 107 shut.

As the wearer of the apparatus 1 exhales, the positive pressure closes the inhalation valve assembly 108 and opens the exhalation valve assembly 107 allowing the exhaled breath to travel through the common airflow passageway 75 through the mask 5, through the common airflow passageway 96, through the exhalation airflow passageway 97, through the exhalation valve opening 105 and out the exhalation discharge passageway 113 into the appropriate monitoring equipment (not shown attached).

The Y-branch design of the airflow tubing assembly allows for proper flow control of inhaled air and exhalation products into and out of the mask 5 while minimizing the restrictions and resistance to normal breathing. Similarly, the use of the common airflow passageway 75 positioned in flow alignment with the mouth minimizes airflow resistance during both inhalation and exhalation. When the mask 5 is secured in position, the mouth of the wearer is positioned in closely spaced relationship with the circular opening 50 of the mask 5 to reduce the dead space volume.

Preferably the gas volume in the chamber 29 of the mask apparatus 1 is below approximately 125 milliliters and even more preferably below 36 milliliters.

It is to be understood that while certain forms of the present invention have been illustrated and described herein, it is not to be limited to the specific forms or arrangement of parts described and shown.

What is claimed and desired to be secured by Letters Patent is as follows:

1. A respiratory apparatus for breath-by-breath ventilatory measurements of a wearer comprising:
   (a) a mask adapted to be secured to the face of a wearer so as to enclose the mouth of the wearer in a mouth enclosing chamber; said mask having sealing means adapted to form a seal between said mask and the face of the wearer about said mouth enclosing chamber; said mask including structural means to conform to the face of the wearer about the mouth of the wearer and to allow the wearer to exhale directly into and inhale directly from said mouth enclosing chamber; and said mask being free of any parts extending into the mouth of the wearer such that the air passes between the mouth of the wearer and the enclosing chamber directly; said enclosing chamber sealing directly against the mouth of the wearer and being sized and shaped to hold substantially only the external parts of the mouth of the wearer such that said structural means maintains dead air space between the mouth and the enclosing chamber at a minimum during use of the apparatus; and (b) a common airflow passageway extending through said mask from an inner surface to an outer surface of said mask and flow communicating with said mouth-enclosing chamber; wherein both inhaled air and exhalation products pass through said common airflow passageway.

2. The respiratory apparatus as described in claim 1 wherein:

(a) said structural means include a biasable sealing flange extending inwards from a peripheral edge of said mask in spaced relation to said inner surface of said mask, said sealing flange adapted to snugly conform to the shape of a face upon which said mask is secured.

3. A respiratory apparatus for breath-by-breath ventilatory measurements of a wearer comprising:

(a) a mask adapted to be secured to the face of a wearer so as to enclose the mouth of the wearer and to form a seal between said mask and the face of the wearer so as to form a mouth enclosing chamber; said mask adapted to allow the wearer to exhale directly into and inhale directly from said mouth-enclosing chamber;

(b) said mask having a common airflow passageway extending through said mask from an inner surface to an outer surface of said mask through which both inhaled air and exhalation products pass; said common airflow passageway flow communicating with said mouth enclosing chamber; and structural means closely conforming to the exterior of a wearer's mouth for positioning said inner surface of said mask in adjacent proximity to the mouth of the wearer during use to limit dead air space within said mouth enclosing chamber, said structural means for positioning also places said common airflow passageway in alignment with and immediately adjacent the wearer's mouth without the use of a mouthpiece; said mask being free of structure extending into a wearer's mouth thereby allowing a wearer to exhale directly into said mouth enclosing chamber; and (c) an airflow tubing assembly secured to said outer surface of said mask; said airflow tubing assembly defining an exhalation passageway and an inhalation passageway each in flow communication with said common airflow passageway; said airflow tubing assembly including airflow regulation means regulating the direction of airflow through said airflow tubing assembly such that exhalation products pass only through said exhalation passageway and inhaled air passes only through said inhalation passageway.

4. The respiratory apparatus as described in claim 3 wherein said seal is formed by:

(a) a biasable sealing flange extending inwards from a peripheral edge of said mask in spaced relation to said inner surface of said mask, said sealing flange including said structural means for conforming about the mouth to the shape of a face upon which said mask is secured.

* * * * *